United States Patent
Otani (10) Patent No.: US 12,220,108 B2
(45) Date of Patent: Feb. 11, 2025

(54) ENDOSCOPE SYSTEM

(71) Applicant: FUJIFILM Corporation, Tokyo (JP)

(72) Inventor: Kenichi Otani, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 40 days.

(21) Appl. No.: 17/323,083

(22) Filed: May 18, 2021

(65) Prior Publication Data

US 2021/0369097 A1 Dec. 2, 2021

(30) Foreign Application Priority Data

Jun. 1, 2020 (JP) ................................. 2020-095488

(51) Int. Cl.
| | | |
|---|---|---|
| *A61B 1/07* | (2006.01) | |
| *A61B 1/00* | (2006.01) | |
| *A61B 1/05* | (2006.01) | |
| *A61B 1/06* | (2006.01) | |
| *H04N 23/73* | (2023.01) | |
| *H04N 25/11* | (2023.01) | |
| *H04N 23/50* | (2023.01) | |

(52) U.S. Cl.
CPC ............ *A61B 1/07* (2013.01); *A61B 1/00186* (2013.01); *A61B 1/051* (2013.01); *A61B 1/0638* (2013.01); *A61B 1/0684* (2013.01); *H04N 23/73* (2023.01); *H04N 25/11* (2023.01); *H04N 23/555* (2023.01)

(58) Field of Classification Search
CPC ... A61B 1/00186; A61B 1/0638; A61B 1/043; H04N 5/2353
See application file for complete search history.

(56) References Cited

U.S. PATENT DOCUMENTS 4,878,113 A * 10/1989 Nakamura ........... A61B 1/0646
348/270
6,099,466 A * 8/2000 Sano .................... A61B 1/0646
600/109

(Continued)

FOREIGN PATENT DOCUMENTS

| JP | H01-280442 A | 11/1989 |
|---|---|---|
| JP | H08-252218 A | 10/1996 |

(Continued)

OTHER PUBLICATIONS

The extended European search report issued by the European Patent Office on Oct. 25, 2021, which corresponds to European Patent Application No. 21176021.0-1126 and is related to U.S. Appl. No. 17/323,083.

(Continued)

*Primary Examiner* — John P Leubecker
*Assistant Examiner* — Jae Woo
(74) *Attorney, Agent, or Firm* — Studebaker & Brackett PC (57) ABSTRACT

An endoscope system includes a light source unit that emits normal light and first specific light having a peak wavelength different from that of each of red light, green light, and blue light included in the normal light, a dichroic filter that transmits first specific return light which is return light from a subject illuminated with the first specific light and that reflects return light from the subject illuminated with the normal light, a CMOS sensor on which the return light of the normal light is incident, and a CMOS sensor on which the first specific return light is incident.

10 Claims, 10 Drawing Sheets

(56) References Cited

U.S. PATENT DOCUMENTS

| | | | |
|---|---|---|---|
| 9,326,666 B2 | 5/2016 | Frangioni | |
| 2002/0004626 A1* | 1/2002 | Abe | A61B 1/042 |
| | | | 600/109 |
| 2006/0173358 A1 | 8/2006 | Xie | |
| 2007/0122345 A1* | 5/2007 | Golijanin | A61B 5/0071 |
| | | | 424/9.6 |
| 2008/0009669 A1* | 1/2008 | Ozawa | A61B 1/00045 |
| | | | 600/101 |
| 2011/0158914 A1 | 6/2011 | Yamada | |
| 2011/0205651 A1 | 8/2011 | Yamano et al. | |
| 2011/0237895 A1* | 9/2011 | Yoshida | A61B 1/0638 |
| | | | 600/180 |
| 2012/0010465 A1* | 1/2012 | Erikawa | A61B 1/0653 |
| | | | 600/109 |
| 2012/0154567 A1 | 6/2012 | Yamaguchi et al. | |
| 2012/0176486 A1* | 7/2012 | Maeda | G01J 3/10 |
| | | | 348/E7.085 |
| 2013/0041221 A1 | 2/2013 | McDowall et al. | |
| 2017/0303775 A1 | 10/2017 | Uchiyama et al. | |
| 2018/0228355 A1* | 8/2018 | Daidoji | A61B 1/0646 |

FOREIGN PATENT DOCUMENTS

| | | |
|---|---|---|
| JP | 2007-143624 A | 6/2007 |
| JP | 2010-268838 A | 12/2010 |
| JP | 2011-131002 A | 7/2011 |
| JP | 2012-016545 A | 1/2012 |
| JP | 2012-125501 A | 7/2012 |
| JP | 2013-111176 A | 6/2013 |
| WO | 2011/007461 A1 | 1/2011 |

OTHER PUBLICATIONS

An Office Action; "Notice of Reasons for Refusal," mailed by the Japanese Patent Office on Apr. 18, 2023, which corresponds to Japanese Patent Application No. 2020-095488 and is related to U.S. Appl. No. 17/323,083; with English language translation.

Communication pursuant to Article 94(3) EPC issued by the European Patent Office on Mar. 18, 2024, which corresponds to European Patent Application No. 21176021.0-1126 and is related to U.S. Appl. No. 17/323,083.

* cited by examiner

ENDOSCOPE SYSTEM

CROSS-REFERENCE TO RELATED APPLICATIONS

This application claims priority under 35 U.S.C § 119(a) to Japanese Patent Application No. 2020-095488 filed on 1 Jun. 2020. The above application is hereby expressly incorporated by reference, in its entirety, into the present application.

BACKGROUND OF THE INVENTION

1. Field of the Invention

The present invention relates to an endoscope system.

2. Description of the Related Art

In the medical field, an endoscope system comprising a light source device, an endoscope, and a processor device has become widespread. The endoscope system illuminates a subject and picks up the image of the return light from the subject. In the endoscope system, an image (observation image) for visually observing the subject can be obtained by illuminating the subject with white light (visible light) including red light, green light, and blue light.

Further, in the endoscope system, the subject is illuminated with near-infrared light (near-infrared rays) having a peak wavelength of about 805 nm and the image of the near-infrared light having a peak wavelength of about 835 nm which is return light (fluorescence) from indocyanine green (ICG) injected into the blood is picked up, and thereby an image (ICG image) for observing the blood flow and the like is obtained.

Furthermore, in the endoscope system, the subject is illuminated with near-ultraviolet light (near-ultraviolet rays, first blue light, and second blue light) and the image of the near-ultraviolet light is picked up by using a property that the light absorption coefficients of oxidized hemoglobin and reduced hemoglobin in the blood vary depending on the wavelength range of illumination light, and thereby an image (blue oxygen saturation image) showing the oxygen saturation of the subject is obtained. Further, the subject is illuminated with the near-infrared light (near-infrared rays, first red light, and second red light) and the image of the near-infrared light is picked up, and thereby an image (red oxygen saturation image) showing the oxygen saturation of the subject is obtained.

In order to acquire both the observation image and the red oxygen saturation image, JP2010-268838A describes a configuration in which the subject is irradiated with illumination light including visible light and infrared light (infrared rays), the return light from the subject is separated (spectrally separated) into a light beam (normal return light) having a wavelength range for obtaining an observation image and a light beam (specific return light (first specific return light and second specific return light)) having a wavelength range for obtaining a red oxygen saturation image, and the images of the light beams incident on image pickup elements different from each other are picked up.

SUMMARY OF THE INVENTION

Incidentally, in JP2010-268838A, there has been a problem that the normal return light may be mixed into the specific return light and thus accurate information cannot be obtained. That is, in JP2010-268838A, the return light from the subject is separated (spectrally separated) by transmitting the normal return light and reflecting the specific return light. However, upon reflecting the specific return light, it is difficult to reflect only the specific return light, and a part of the normal return light may be reflected together with the specific return light. Therefore, accurate information cannot be obtained due to the mixing of such noise (normal return light).

The present invention has been made in view of the above backgrounds, and an object thereof is to provide an endoscope system capable of preventing noise (normal return light) from being mixed into specific return light and acquiring accurate information.

In an endoscope system that illuminates a subject and picks up an image of return light from the subject, the endoscope system according to an aspect of the present invention comprises a light source that emits normal light consisting of white light including red light, green light, and blue light, and first specific light having a peak wavelength different from a peak wavelength of each of the red light, the green light, and the blue light; a spectral element that transmits first specific return light which is return light from the subject illuminated with the first specific light and that reflects normal return light which is return light from the subject illuminated with the normal light; a normal image pickup element on which the normal return light is incident; and a specific image pickup element on which the first specific return light is incident.

The first specific light may include first blue light having a wavelength of 473 nm, and the normal light may include second blue light having a wavelength of 445 nm.

The light source may emit second specific light having a peak wavelength different from a peak wavelength of each of the red light, the green light, the blue light, and the first specific light, the spectral element may transmit second specific return light which is return light from the subject illuminated with the second specific light, and the second specific return light may be incident on the specific image pickup element.

The second specific light may include excitation light having a wavelength of 805 nm, and the second specific return light may include fluorescence having a wavelength of 835 nm excited with the excitation light.

An optical element that cuts the excitation light may be provided between the spectral element and the specific image pickup element.

The optical element may be a notch filter.

The normal light may include first red light having a wavelength of 640 nm, and the second specific light may include second red light having a wavelength of 800 nm.

A light amount controller that controls an amount of the first specific light to any one of a plurality of stages, may be provided.

The specific image pickup element may change an exposure time to control brightness of a pickup image.

The specific image pickup element may be a monochrome image pickup sensor.

The spectral element may be a dichroic filter.

With the endoscope system according to the aspect of the present invention, it is possible to prevent noise (normal return light) from being mixed into the specific return light and acquire accurate information.

DESCRIPTION OF THE PREFERRED EMBODIMENTS

First Embodiment

Figure 1:
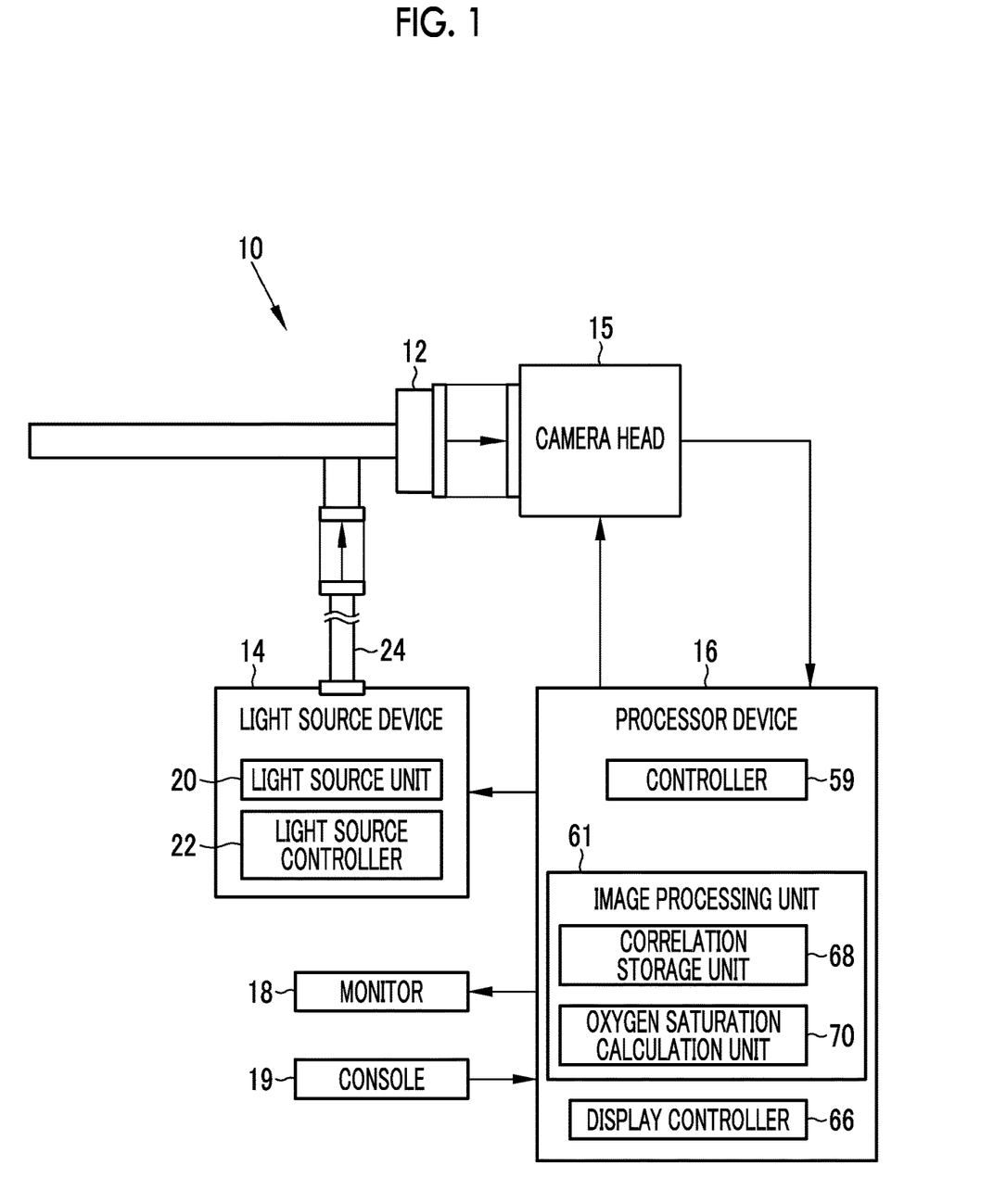
FIG. 1 is a configuration diagram of an endoscope system.

As shown in FIG. 1, an endoscope system 10 comprises an endoscope 12, a light source device 14, a camera head 15, a processor device 16, a monitor 18, and a console 19.

The endoscope 12 is hard and elongated, and is inserted into a subject to be examined An optical system for forming a subject image and an optical system for irradiating the subject with illumination light are provided inside the endoscope 12. The light source device 14 generates illumination light. The camera head 15 picks up an image of the subject. The processor device 16 performs system control, image processing, and the like of the endoscope system 10. The monitor 18 is a display unit that displays the image picked up by the endoscope 12. The console 19 is an input device which is used to input settings to the processor device 16 and the like.

The light source device 14 comprises a light source unit 20 that emits illumination light, and a light source controller 22 (light amount controller) that controls the operation of the light source unit 20.

The light source unit 20 emits illumination light that illuminates the subject, excitation light that is used to emit the illumination light, or the like. The light source unit 20 includes, for example, a light source of a laser diode (hereinafter, referred to as an LD), a light emitting diode (LED), a xenon lamp, or a halogen lamp, and emits at least white illumination light or excitation light that is used to emit the white illumination light. The white color includes so-called pseudo white color, which is substantially the same as the white color in the image pickup of the subject using the endoscope 12.

Further, the light source unit 20 includes, as necessary, a phosphor that emits light by irradiation with excitation light, or an optical filter that adjusts a wavelength range, a spectrum, an amount of light, or the like of illumination light or excitation light. In addition, the light source unit 20 can emit light necessary for picking up an image which is used to calculate biological information such as oxygen saturation of hemoglobin contained in the subject.

Figure 4:
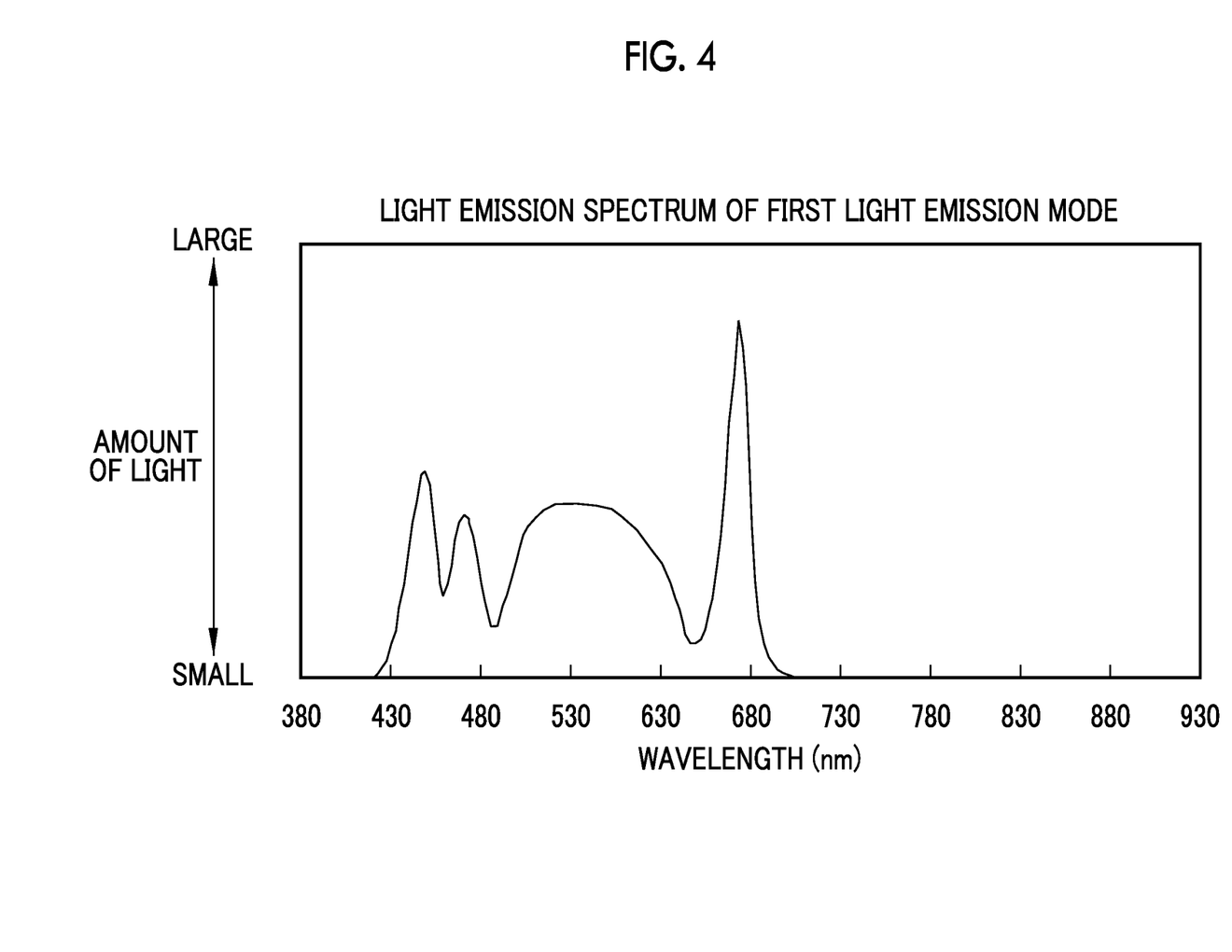
FIG. 4 is a graph showing a spectrum of a first light emission mode.
Figure 5:
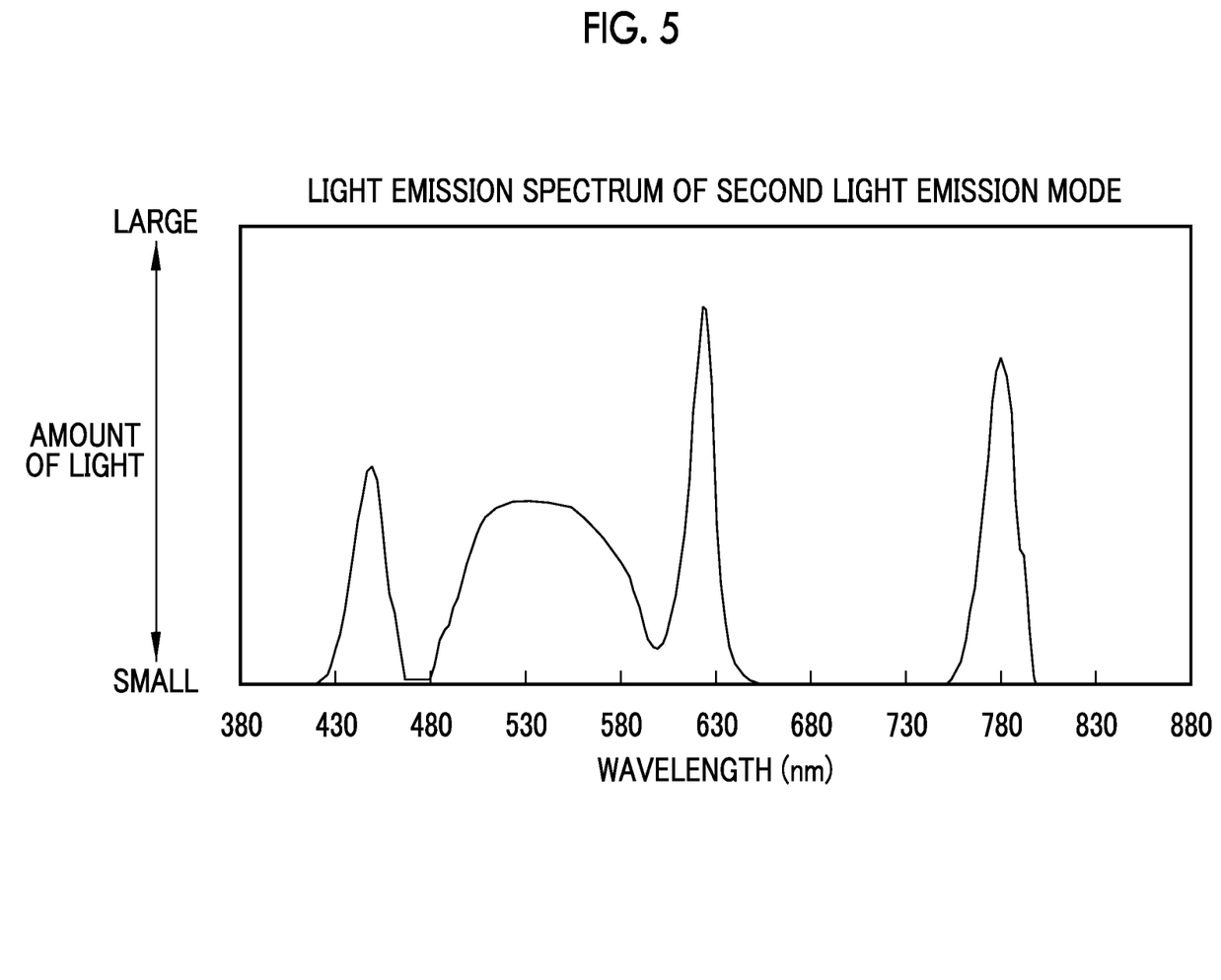
FIG. 5 is a graph showing a spectrum of a second light emission mode.

In the present embodiment, the light source unit 20 has a first LED that emits blue light (normal light, blue light, and second blue light) having a center wavelength of about 445 nm (see FIGS. 4 and 5), and a second LED that emits blue light (first specific light and first blue light) having a center wavelength of about 473 nm (see FIG. 5). Further, the light source unit 20 includes a third LED that emits green light (normal light and green light) having a center wavelength of about 540 nm (see FIGS. 4 and 5), and a fourth LED that emits red light (normal light, red light, and first red light) having a center wavelength of about 640 nm (see FIGS. 4 and 5). Furthermore, the light source unit 20 includes a fifth LED that emits near-infrared light (second specific light) having a center wavelength of about 780 nm (see FIG. 5). In the present embodiment, the second specific light includes excitation light having a wavelength of about 805 nm (excitation light of ICG).

Figure 2:
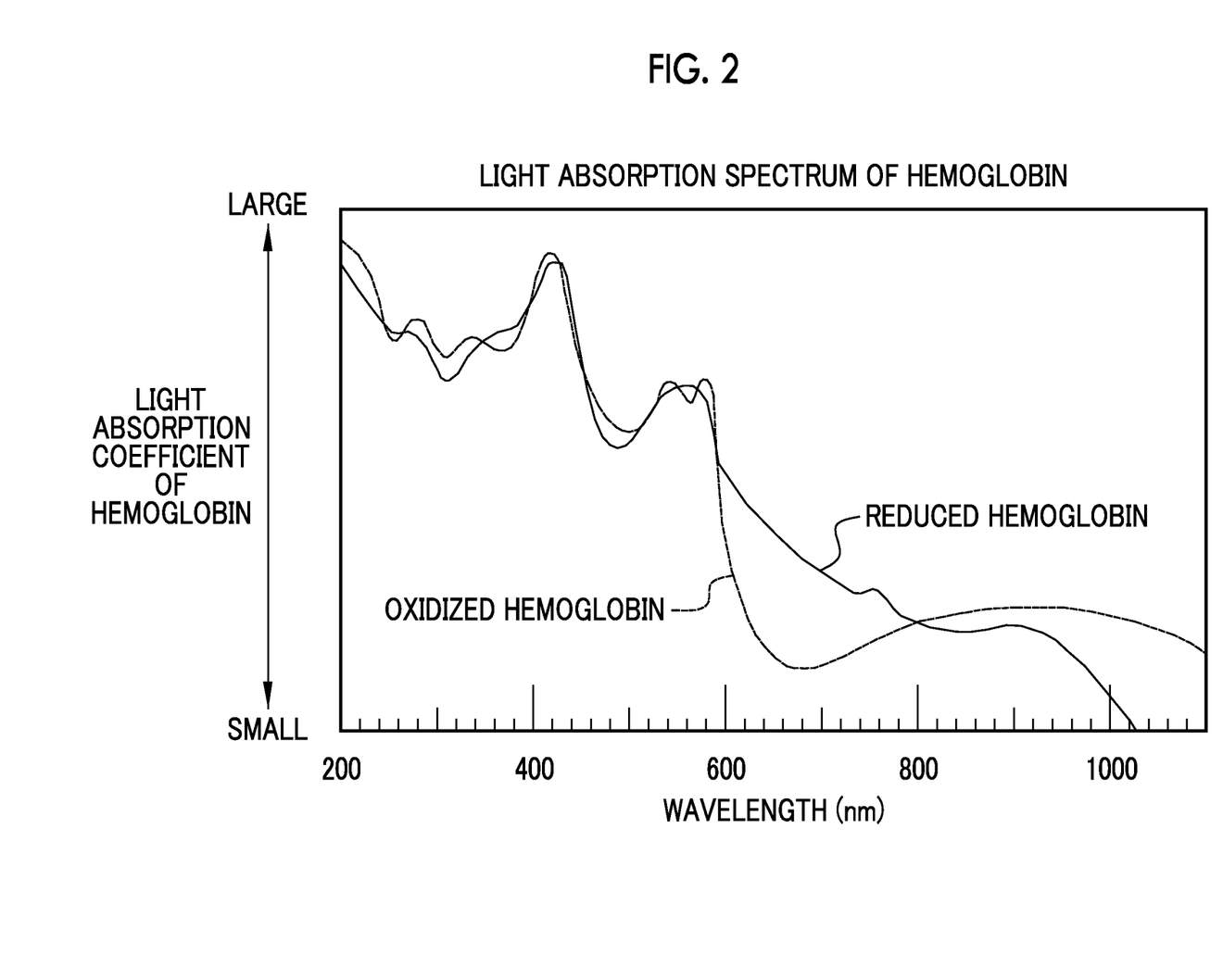
FIG. 2 is a graph showing light absorption coefficients of hemoglobin and oxidized hemoglobin.

Here, the first blue light and the second blue light are light necessary for generating an image (blue oxygen saturation image) showing biological information such as oxygen saturation of hemoglobin contained in the subject. That is, as shown in FIG. 2, a wavelength of about 445 nm which is a center wavelength of the second blue light is a wavelength at which the light absorption coefficients of oxidized hemoglobin and reduced hemoglobin hardly differ from each other. A wavelength of about 473 nm which is a center wavelength of the first blue light is a wavelength at which the difference between the light absorption coefficients of oxidized hemoglobin ($HbO_2$) and reduced hemoglobin (Hb) is approximately maximized. Accordingly, the subject is irradiated with illumination light including the first blue light and the second blue light, the image of the subject is picked up, and the difference between the light absorption coefficients of the first blue light and the second blue light is examined, so that biological information such as oxygen saturation of hemoglobin contained in the subject can be calculated and the blue oxygen saturation image can be generated based on the calculated value.

Figure 3:
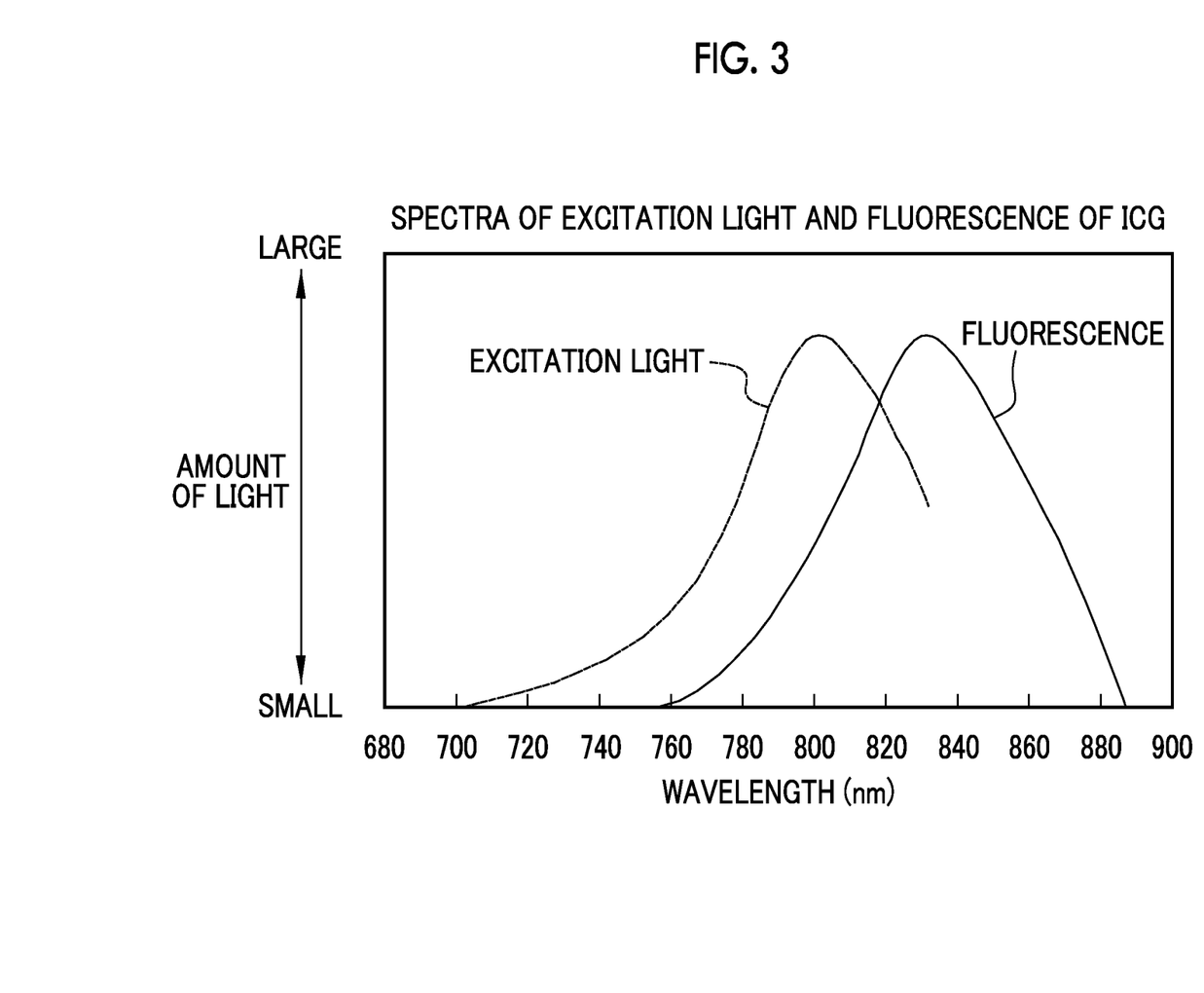
FIG. 3 is a graph showing spectra of excitation light and fluorescence of ICG.

Further, the second specific light, that is, the light including the excitation light of ICG having a wavelength of about 805 nm is light necessary for picking up an image (ICG image) used to observe biological information such as a blood flow. That is, as shown in FIG. 3, fluorescence having a peak wavelength of about 835 nm can be obtained from ICG as return light (return light of ICG) by illumination with the excitation light having a peak wavelength of about 805 nm (excitation light of ICG). Therefore, the subject such as blood (blood vessel) into which ICG is injected is illuminated with illumination light including the second specific light, the image of return light is picked up, and the ICG image picked up is observed, so that biological information such as a blood flow can be obtained.

As shown in FIGS. 4 and 5, in the present embodiment, the light source unit 20 emits light in two kinds of light emission modes of a first light emission mode for generating an observation image and a blue oxygen saturation image, and a second light emission mode for generating an observation image and an ICG image, by the control of the light source controller 22 described later. As shown in FIG. 4, the first light emission mode is a light emission mode in which the first to fourth LEDs are emitted, that is, a light emission mode in which the subject is illuminated with white normal light consisting of second blue light (blue light), green light, and red light, and first specific light consisting of first blue light. On the other hand, as shown in FIG. 5, the second light emission mode is a light emission mode in which the first LED and the third to fifth LEDs are emitted, that is, a light emission mode in which the subject is illuminated with white normal light consisting of second blue light (blue light), green light, and red light, and second specific light including excitation light having a wavelength of about 805 nm.

Returning to FIG. 1, the light source controller 22 controls the on or off, the amount of light emitted of each light source constituting the light source unit 20, and emits illumination light in the two light emission modes of the first light emission mode (see FIG. 4) and the second light emission mode (see FIG. 5) described above. The illumination light emitted by the light source unit 20 is incident on the endoscope 12 through a light guide 24, is guided to the distal end of the endoscope 12 through the optical system (optical system for irradiating the subject with illumination light) built in the endoscope 12, and is emitted from the distal end of the endoscope 12 toward the subject. After that, the subject is irradiated with the illumination light, and the return light from the subject is guided to the camera head 15 through the optical system (optical system for forming a subject image) built in the endoscope 12.

Figure 6:
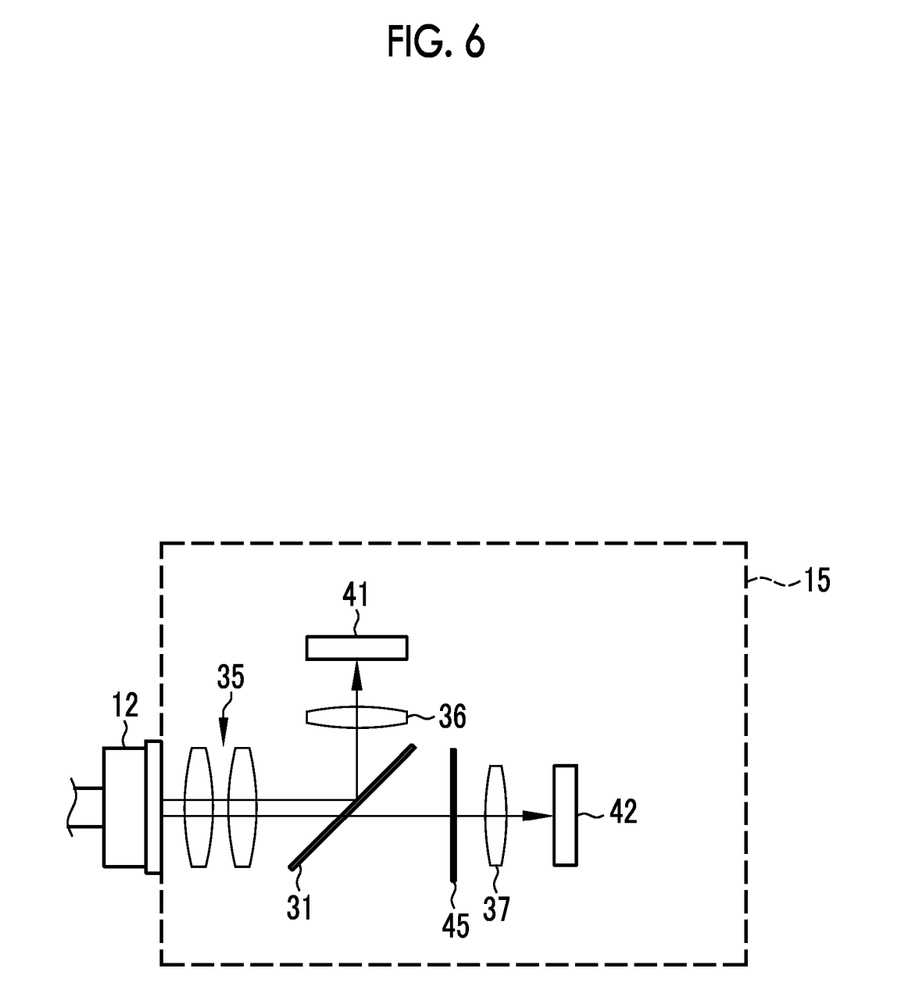
FIG. 6 is a configuration diagram of a camera head.

As shown in FIG. 6, the camera head 15 comprises a dichroic filter (spectral element) 31, image-forming optical systems 35, 36, and 37, complementary metal oxide semiconductor (CMOS) sensors 41 (normal image pickup element) and 42 (specific image pickup element), and a notch filter 45 (optical element).

Figure 7:
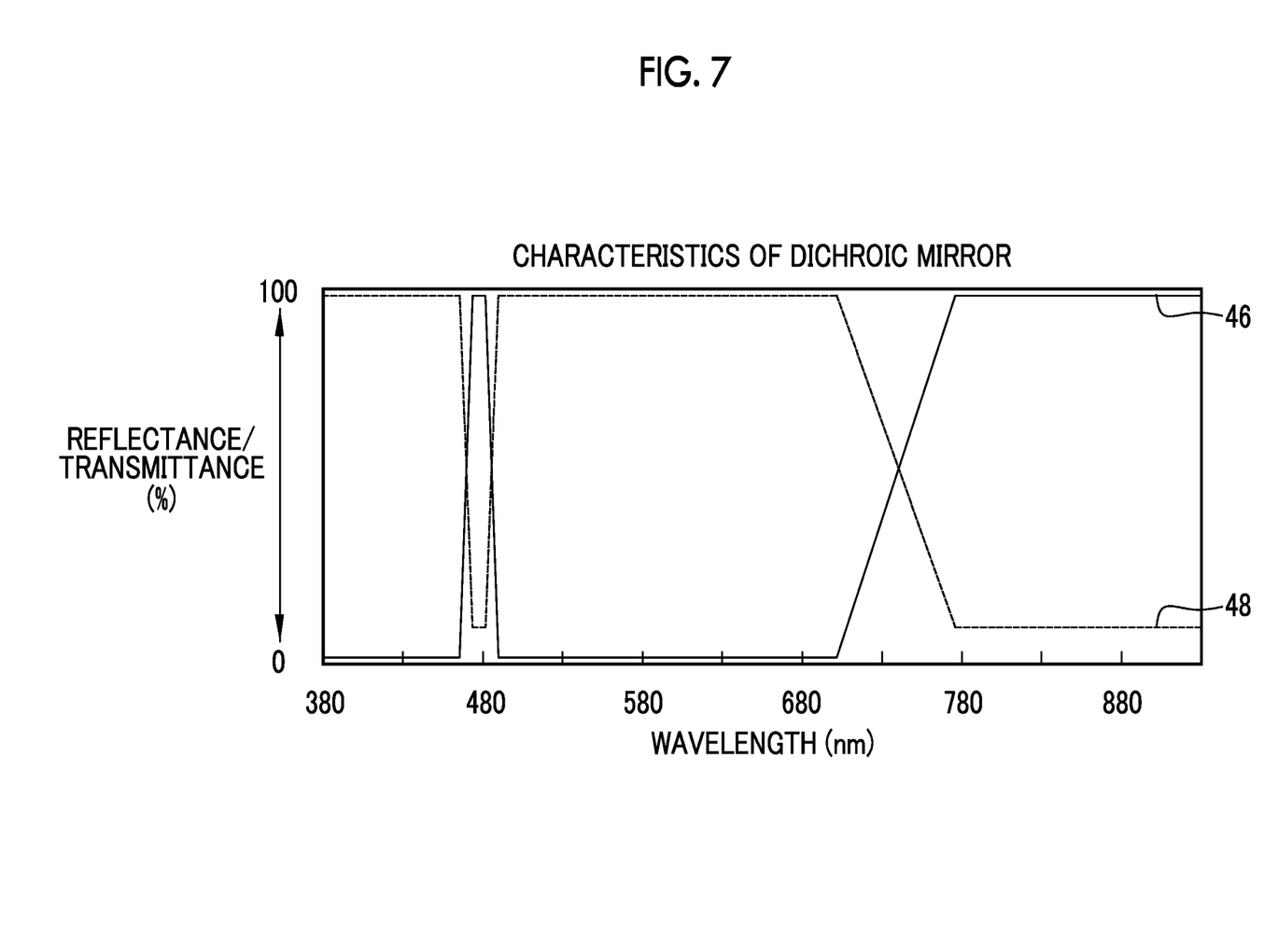
FIG. 7 is a characteristic diagram of a dichroic filter.

As shown by the solid line 46 in FIG. 7, the dichroic filter 31 has a property that transmits the return light (first specific return light) of the first specific light with which the subject is irradiated (in the present embodiment, first blue light having a center wavelength of about 473 nm) and the return light (second specific return light) (in the present embodiment, fluorescence having a peak wavelength of about 835 nm) of the second specific light with which the subject is irradiated (in the present embodiment, excitation light having a peak wavelength of about 805 nm).

On the other hand, as shown by the broken line 48 in FIG. 7, the dichroic filter 31 has a property that reflects the return light of the normal light with which the subject is irradiated (normal return light), specifically, the return light of the blue light (in the present embodiment, second blue light having a center wavelength of about 445 nm), the return light of the green light (in the present embodiment, green light having a center wavelength of about 540 nm), and the return light of the red light (in the present embodiment, red light having a center wavelength of about 640 nm).

Here, in the spectral element including the dichroic filter 31, the transmittance of light in a desired wavelength range can be generally suppressed to almost 0%, more specifically, to about 0.1% (see the solid line 46 in FIG. 7). On the other hand, it is difficult to set the reflectance of light in a desired wavelength range to almost 0% and the dichroic filter 31 has a property that light in a wavelength range which is not intended to be reflected may be reflected by about 2% (see the broken line 48 in FIG. 7).

In this way, the light reflected by the dichroic filter 31 may also include the light in a wavelength range which is not intended to be reflected. Therefore, assuming that the return light of the first and second specific light is reflected by the dichroic filter, the return light of the normal light may be mixed into the return light of the first and second specific light. On the other hand, the present invention has a configuration in which the return light of the first and second specific light is transmitted through the dichroic filter 31. As a result, it is possible to prevent the return light of the normal light from being mixed into the return light of the first and second specific light (compared with the configuration in which the return light of the first and second specific light is reflected by the dichroic filter, it is possible to reduce the mixing of the return light of the normal light to about 1/20).

In FIG. 5, the light reflected by the dichroic filter 31, that is, the return light of the normal light is incident on the CMOS sensor 41. The image of the return light of the normal light is formed on the image pickup surface of the CMOS sensor 41 by the image-forming optical systems 35 and 36 in the process of being incident on the CMOS sensor 41.

Figure 8:
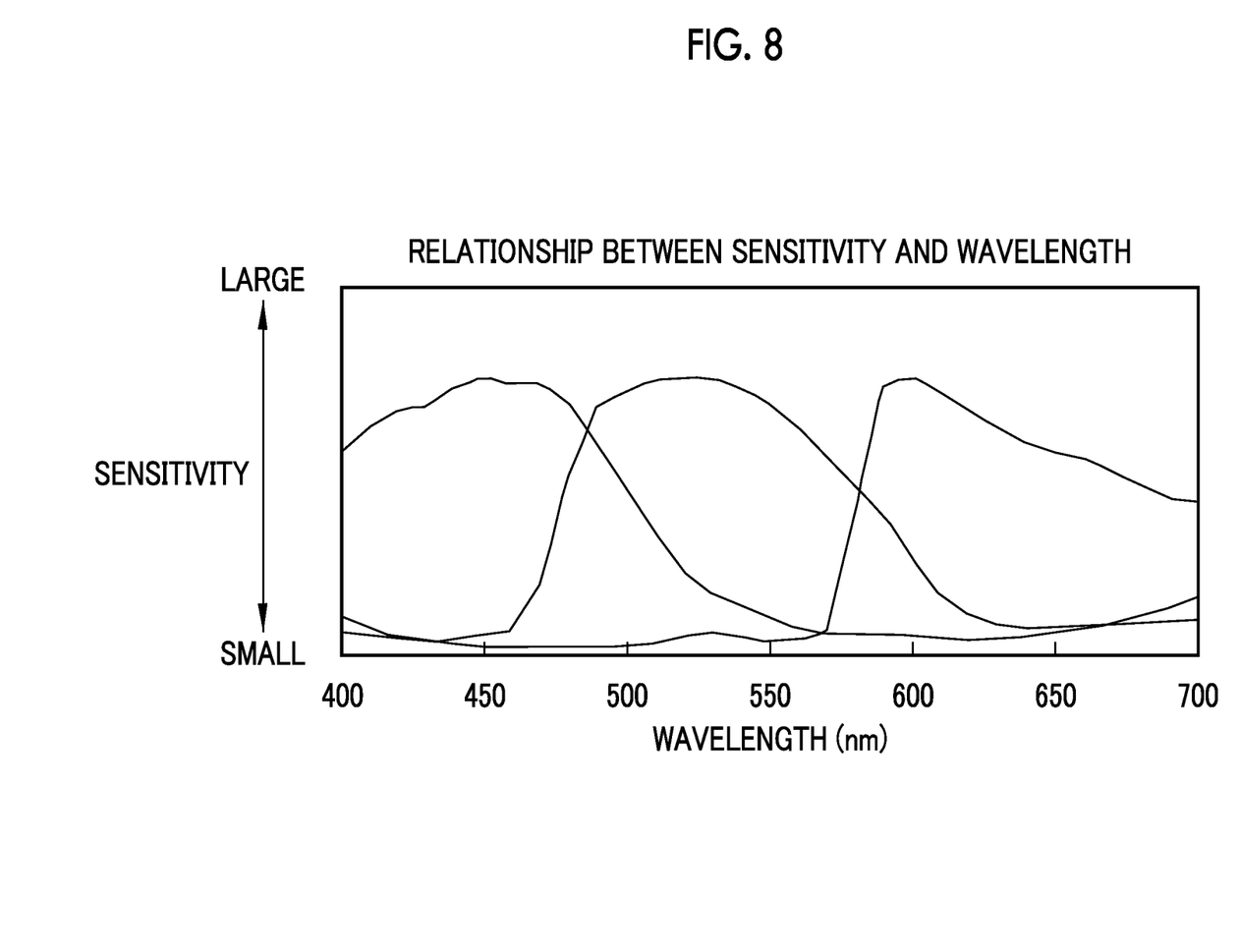
FIG. 8 is an explanatory diagram showing a relationship between a sensitivity and a wavelength of a CMOS sensor.

As shown in FIG. 8, the CMOS sensor 41 is a color image pickup sensor in which three kinds of pixels are arranged on the image pickup surface thereof. The three kinds of pixels include a blue image pickup pixel having the sensitivity to the return light of the blue light (capable of picking up the image of the return light of the blue light), a green image pickup pixel having the sensitivity to the return light of the green light (capable of picking up the image of the return light of the green light), and a red image pickup pixel having the sensitivity to the return light of the red light (capable of picking up the image of the return light of the red light). A full color image showing the amount of light of the return light of the normal light (the return light of each of blue light, green light, and red light) can be obtained by the image pickup by the CMOS sensor 41.

Returning to FIG. 5, the light transmitted through the dichroic filter 31, that is, each return light of the first and second specific light is incident on a CMOS sensor 42. The image of each return light of the first and second specific light is formed on the image pickup surface of the CMOS sensor 42 by the image-forming optical systems 35 and 37 in the process of being incident on the CMOS sensor 42. Further, a notch filter 45 is disposed between the dichroic filter 31 and the CMOS sensor 42, and the excitation light of ICG (peak wavelength of about 805 nm) among the light transmitted through the dichroic filter 31 is cut by the notch filter 45. The function of the notch filter 45 may be imparted to the dichroic filter 31, and the notch filter 45 may be removed. Further, instead of or in addition to the dichroic filter 31, an optical element such as a beam splitter that splits a light beam into two or more light beams may be used. Furthermore, instead of or in addition to the notch filter 45, an optical element such as a beam splitter that splits a light beam into two or more light beams may be used.

Figure 9:
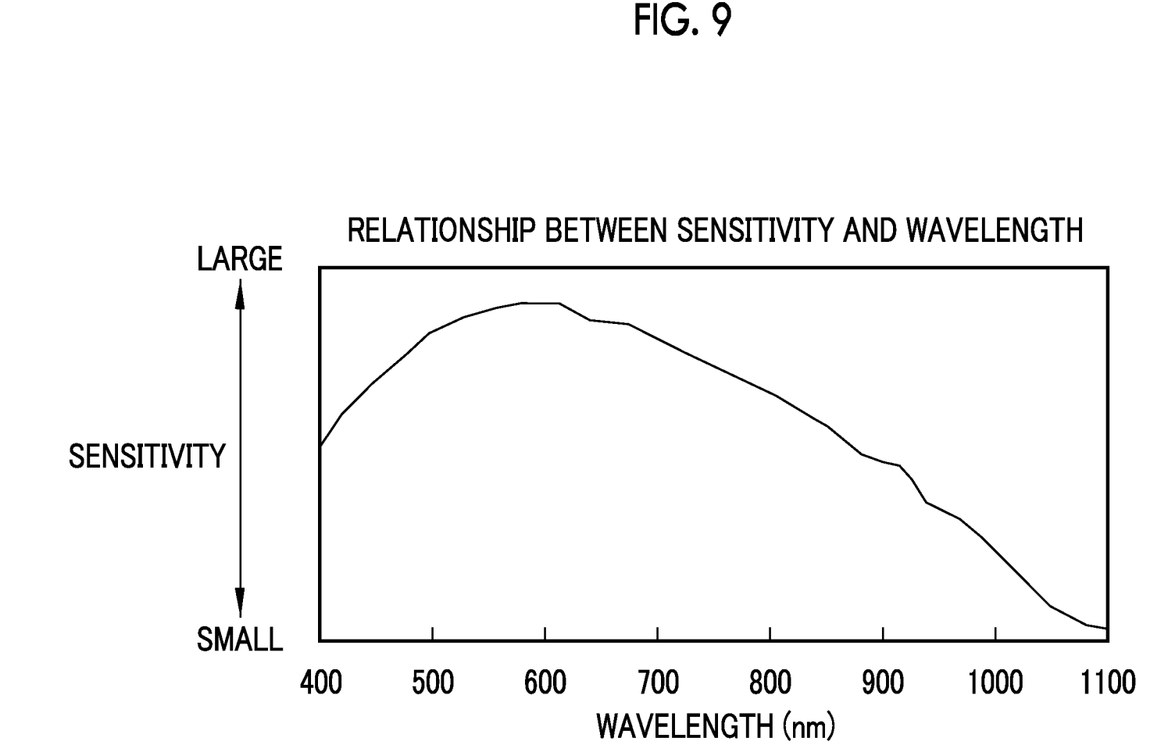
FIG. 9 is an explanatory diagram showing a relationship between a sensitivity and a wavelength of another CMOS sensor.

As shown in FIG. 9, the CMOS sensor 42 is a monochrome image pickup sensor consisting of one kind of pixel. The one kind of pixel has at least the sensitivity to each return light of the first and second specific light (capable of picking up the image of each return light of the first and second specific light). A monochrome image showing the amount of the return light of the first specific light or the return light of the second specific light can be obtained by the image pickup by the CMOS sensor 42.

In the present embodiment, an observation image and a blue oxygen saturation image, or an observation image and an ICG image can be obtained by the image pickup by the CMOS sensors 41 and 42.

Specifically, the light source unit 20 emits light in the first light emission mode (see FIG. 4), and thereby the return light of the normal light is incident on the CMOS sensor 41. Therefore, an observation image can be obtained by the image pickup by the CMOS sensor 41. Further, the light source unit 20 emits light in the first light emission mode, and thereby the return light of the second blue light is incident on the CMOS sensor 41 and the return light of the first specific light (first blue light) is incident on the CMOS sensor 42. Therefore, a blue oxygen saturation image can be obtained by the image pickup by the CMOS sensors 41 and 42. The observation image and the blue oxygen saturation image can be obtained at the same time (obtained from the images picked up at the same timing). Therefore, in a case where the two images are displayed in a superimposed manner and the like later, it is not necessary to perform processing such as registration of the two images.

On the other hand, the light source unit 20 emits light in the second light emission mode (see FIG. 5), and thereby the return light of the normal light is incident on the CMOS sensor 41 as in the case where the light source unit 20 emits light in the first light emission mode. Therefore, an observation image can be obtained by the image pickup by the CMOS sensor 41. Further, the light source unit 20 emits light in the second light emission mode, and thereby the return light (fluorescence of ICG) of the second specific light (excitation light of ICG) is incident on the CMOS sensor 42. Accordingly, an ICG image can be obtained by the image pickup by the CMOS sensor 42. In this case, the observation image and the ICG image can also be obtained at the same time (obtained from the images picked up at the same timing), as in the case of the observation image and the blue oxygen saturation image. For this reason, in a case where the two images are displayed in a superimposed manner and the like later, it is not necessary to perform processing such as registration of the two images.

Returning to FIG. 1, the processor device 16 has a controller 59, an image processing unit 61, and a display controller 66.

The controller 59 integrally controls the endoscope system 10 such as illumination control (control of the light source device 14) and imaging control (control of the camera head 15). In a case where various settings are input by using the console 19 or the like, each unit of the endoscope system 10, such as the light source controller 22, the camera head 15, and/or the image processing unit 61 receives the setting from the controller 59.

In the present embodiment, the controller 59 drives each unit of the endoscope system 10 in two modes of a first mode and a second mode. The first mode is a mode in which the light source unit 20 emits light in the first light emission mode, the images are picked up by the CMOS sensors 41 and 42, and an observation image and a blue oxygen saturation image are acquired. On the other hand, the second mode is a mode in which the light source unit 20 emits light in the second light emission mode, the images are picked up by the CMOS sensors 41 and 42, and an observation image and an ICG image are acquired.

In the image pickup, the controller 59 drives each of the CMOS sensors 41 and 42 to continuously pick up the images in a preset image pickup cycle (frame rate). Further, in the image pickup, the controller 59 independently controls the shutter speed of the electronic shutter of each of the CMOS sensors 41 and 42, that is, the exposure period, for each of the CMOS sensors 41 and 42. As a result, the brightness of the images obtained by the CMOS sensor 41 and/or the CMOS sensor 42 is controlled (adjusted).

In the present embodiment, an example in which the first specific light (first blue light) is emitted in the first mode and the first specific light is not emitted in the second mode, that is, a configuration in which the amount of the first specific light is changed in two stages has been described, but a configuration in which the amount of the first specific light is changed in three or more stages may be employed.

The image processing unit 61 generates the observation image and the blue oxygen saturation image in the first mode and generates the observation image and the ICG image in the second mode by using the images picked up by the CMOS sensors 41 and 42. The image processing unit 61 generates the observation image by using a signal of the image picked up by the CMOS sensor 41. The observation image is an image obtained by picking up the image of the return light of the normal light, and is an image which is the same as an image visually recognized in a case where the subject is irradiated with white light.

Further, the image processing unit 61 is provided with a correlation storage unit 68 and an oxygen saturation calculation unit 70. Correlation information indicating a correlation between oxygen saturation, and signal values and/or a ratio of signal values indicating the amounts of the return light from the second blue light included in the image picked up by the CMOS sensor 41 and the return light from the first blue light included in the image picked up by the CMOS sensor 42, is stored in the correlation storage unit 68. The oxygen saturation calculation unit 70 reads out the correlation information from the correlation storage unit 68 and calculates the oxygen saturation by using the correlation information. In the first mode, the image processing unit 61 operates the correlation storage unit 68 and the oxygen saturation calculation unit 70 to calculate the oxygen saturation value at each pixel position of the images picked up by the CMOS sensors 41 and 42, so that an oxygen saturation image (in the present embodiment, blue oxygen saturation image) representing the value in color is generated.

Furthermore, in the second mode, the image processing unit 61 generates an ICG image in which a signal value of the image picked up by the CMOS sensor 42 is represented by color. In this way, the generated observation image, blue oxygen saturation image, and ICG image are output to and displayed on the monitor 18 through the display controller 66.

Second Embodiment

In the first embodiment, the observation image and the ICG image are generated in the second mode. On the other hand, in the second embodiment, an observation image and a red oxygen saturation image are generated in the second mode. In the first mode, the observation image and the blue oxygen saturation image are generated in the same procedures as in the first embodiment. Therefore, in the second embodiment, the description of the first mode will not be repeated.

In the second embodiment, the light source unit 20 has the same configuration as in the first embodiment and in the second mode, the light source unit 20 emits light in the second light emission mode (see FIG. 5). The illumination light emitted by the light source unit 20 in the second mode includes first red light which is light having a center wavelength of about 640 nm. Further, the illumination light emitted by the light source unit 20 in the second mode includes second red light (second specific light) having a center wavelength of about 800 nm.

On the other hand, in the second embodiment, a camera head in which the notch filter 45 is removed from the camera head 15 shown in FIG. 5 may be used as a camera head. Thereby, in the second embodiment, the reflected light of the second red light reflected by the subject (return light and second specific return light) is incident on the CMOS sensor 42.

In the second embodiment, the return light of the normal light including the return light of the first red light among the return light from the subject is reflected by the dichroic filter 31 and is incident on the CMOS sensor 41. Further, the return light of the second red light is transmitted through the dichroic filter 31 and is incident on the CMOS sensor 42.

Here, the first red light and the second red light are light necessary for generating an image (red oxygen saturation image) showing biological information such as oxygen saturation of hemoglobin contained in the subject. That is, as shown in FIG. 2, the light absorption coefficient of the first red light (center wavelength of about 640 nm) and the light absorption coefficient of the second red light (center wavelength of about 800 nm) vary depending on the oxidized hemoglobin ($HbO_2$) and the reduced hemoglobin (Hb). Therefore, the subject is irradiated with the illumination light including the first red light and the second red light, the image of the subject is picked up, so that the oxygen saturation can be calculated. As a result, a red oxygen saturation image can be generated by using the calculated oxygen saturation.

The red light (first red light, second red light, and the like) has a wavelength longer than that of the blue light (first blue light, second blue light, and the like), and has a property that the red light reaches the deeper side than the blue light (deeper part of the subject). Therefore, the blue light is suitable for acquiring biological information on the surface part of the subject, whereas the red light is suitable for acquiring biological information on the deep part of the subject. In other words, the blue oxygen saturation image generated by using blue light more appropriately shows the oxygen saturation of blood flowing through the blood vessels in the surface part of the subject, whereas the red oxygen saturation image generated by using red light more appropriately shows the oxygen saturation of blood flowing through the blood vessels in the deep part of the subject.

In the second embodiment, in addition to the correlation information indicating the correlation between oxygen saturation, and signal values and/or a ratio of signal values indicating the amounts of the return light of the above-described first and second blue light, correlation information indicating a correlation between oxygen saturation, and signal values and/or a ratio of signal values indicating the amounts of the return light of the first and second red light is stored in the correlation storage unit 68 (see FIG. 1). The oxygen saturation value at each pixel position is calculated from the return light of the first and second red light by using the correlation information. As a result, an oxygen saturation image (red oxygen saturation image) showing the calculated oxygen saturation value in color is generated.

In the first and second embodiments described above, an example in which a dichroic filter is used as a spectral element has been described, but the present invention is not limited thereto. For example, an optical member different from the dichroic filter, such as a prism, a diffraction grating, and/or a bandpass filter, may be used as a spectral element. Of course, a plurality of optical members may be combined to function as a spectral element.

Figure 10:
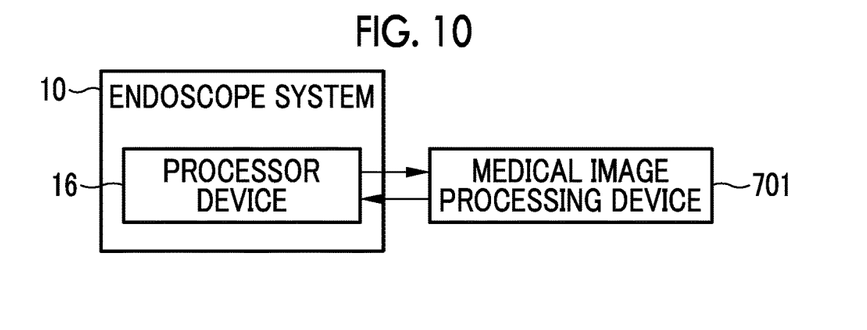
FIG. 10 is an explanatory diagram showing a relationship between another endoscope system and an image processing device.
Figure 11:
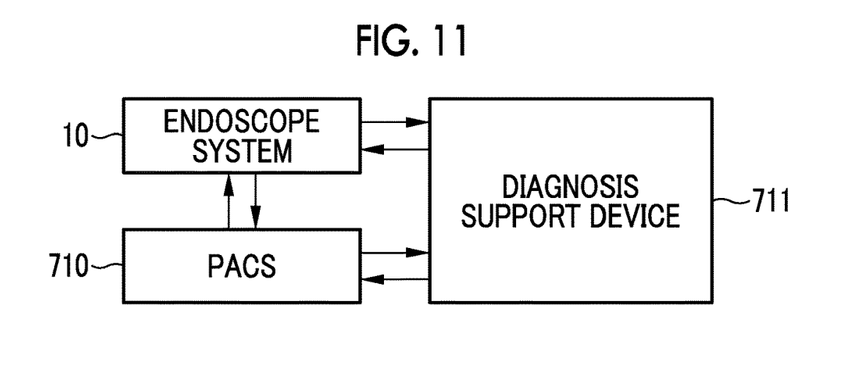
FIG. 11 is an explanatory diagram showing a relationship between still another endoscope system and PACS, and a diagnosis support device.
Figure 12:
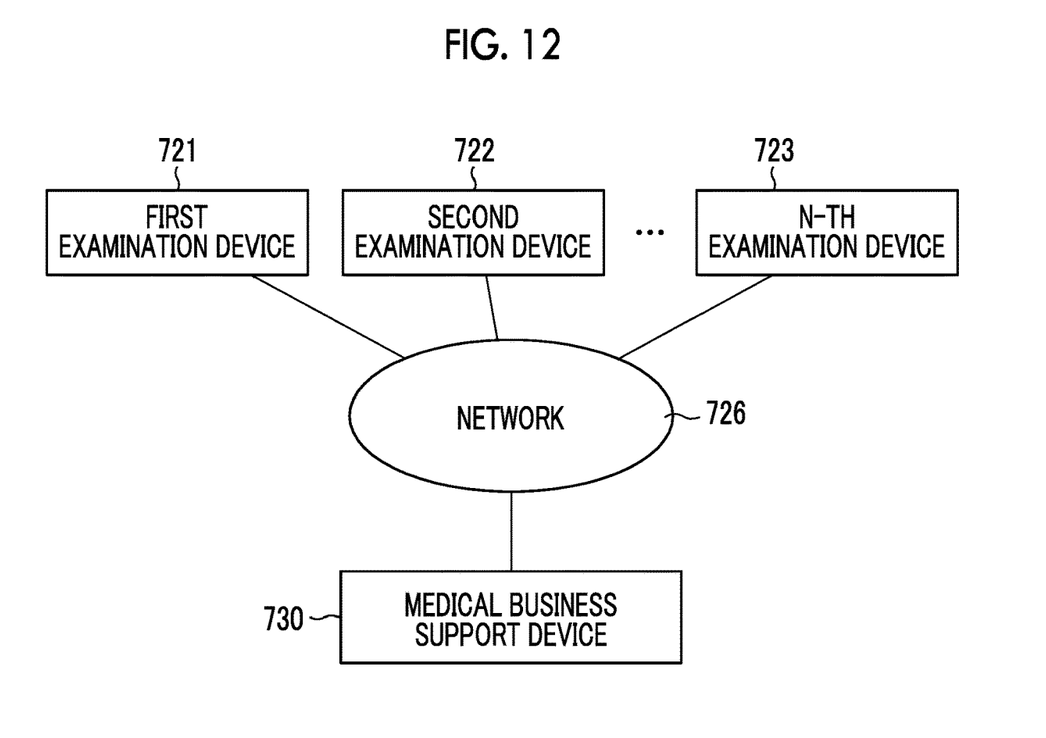
FIG. 12 is an explanatory diagram showing a relationship between various examination devices and a medical business support device.

Further, in the first and second embodiments described above, an example in which the image processing unit 61 and the controller 59 are provided in the endoscope system 10 has been described, but the present invention is not limited thereto. As shown in FIG. 10, a part or all of the image processing unit 61 and/or the controller 59 of the endoscope system 10 can be provided, for example, in a medical image processing device 701 that associates with the endoscope system 10 through the communication with the processor device 16. Further, as shown in FIG. 11, a part or all of the image processing unit 61 and/or the controller 59 of the endoscope system 10 can be provided in a diagnosis support device 711 that acquires the image picked up by the endoscope 12, for example, directly from the endoscope system 10 or indirectly from picture archiving and communication systems (PACS) 710. Further, as shown in FIG. 12, a part or all of the image processing unit 61 and/or the controller 59 of the endoscope system 10 can be provided in a medical business support device 730 that is connected to various examination devices including the endoscope system 10, such as a first examination device 721, a second examination device 722, . . . , and an N-th examination device 723 through the network 726.

EXPLANATION OF REFERENCES

10: Endoscope system
12: Endoscope
14: Light source device
15: Camera head
16: Processor device
18: Monitor
19: Console
20: Light source unit
22: Light source controller (light amount controller)
24: Light guide
31: Dichroic filter (spectral element)
35, 36, 37: Image-forming optical system
41: CMOS sensor (normal image pickup element)
42: CMOS sensor (specific image pickup element)
45: Notch filter
46: Solid line: line showing relationship between wavelength and transmittance of transmitted light.
48: Broken line: line showing relationship between wavelength and reflectance of reflected light.
59: controller
61: Image processing unit
66: Display controller
68: Correlation storage unit
70: Oxygen saturation calculation unit
701: Medical image processing device
710: PACS
711: Diagnosis support device
721: First examination device
722: Second examination device
723: N-th examination device
726: Network
730: Medical business support device

What is claimed is:

1. An endoscope system that illuminates a subject and picks up an image of return light from the subject, the endoscope system comprising:
   a light source that emits normal light consisting of white light including red light, green light, and blue light, and first specific light having a single peak wavelength different from a peak wavelength of each of the red light, the green light, and the blue light;
   a spectral element that transmits first specific return light which is return light from the subject illuminated with the first specific light and that reflects normal return light which is return light from the subject illuminated with the normal light, the spectral element including one or more of a dichroic filter, a prism, a diffraction grating, and a bandpass filter;

a normal image pickup element on which the normal return light is incident;

a specific image pickup element on which the first specific return light is incident; and a processor configured to generate an observation image and an oxygen saturation image, the observation image being generated from signal values of a normal image picked up by the normal image pickup element, the oxygen saturation image being generated from oxygen saturation calculated using both the signal values of the normal image picked up by the normal image pickup element and signal values of a specific image picked up by the specific image pickup element, wherein the light source emits both the normal light and the first specific light simultaneously, the normal image pickup element and the specific image pickup element simultaneously pickup images to acquire both the normal image and the specific image at the same time, and the processor is configured to use both the simultaneously captured normal and specific images to generate the oxygen saturation image.

2. The endoscope system according to claim 1, wherein the first specific light includes first blue light having a wavelength of 473 nm, and the normal light includes second blue light having a wavelength of 445 nm.

3. The endoscope system according to claim 1, wherein the light source emits second specific light having a peak wavelength different from a peak wavelength of each of the red light, the green light, the blue light, and the first specific light, the spectral element transmits second specific return light which is return light from the subject illuminated with the second specific light, and the second specific return light is incident on the specific image pickup element.

4. The endoscope system according to claim 3, wherein the second specific light includes excitation light having a wavelength of 805 nm, and the second specific return light includes fluorescence having a wavelength of 835 nm excited with the excitation light.

5. The endoscope system according to claim 4, wherein an optical element that cuts the excitation light is provided between the spectral element and the specific image pickup element, the optical element including one or more of a notch filter and a beam splitter.

6. The endoscope system according to claim 5, wherein the optical element is a notch filter.

7. The endoscope system according to claim 3, wherein the normal light includes first red light having a wavelength of 640 nm, and the second specific light includes second red light having a wavelength of 800 nm.

8. The endoscope system according to claim 1, wherein the specific image pickup element changes an exposure time to control brightness of a pickup image.

9. The endoscope system according to claim 1, wherein the specific image pickup element is a monochrome image pickup sensor.

10. The endoscope system according to claim 1, wherein the spectral element is a dichroic filter.

* * * * *